(12) United States Patent
Marmulla et al.

(10) Patent No.: US 7,079,885 B2
(45) Date of Patent: Jul. 18, 2006

(54) METHOD AND DEVICE FOR INSTRUMENT, BONE SEGMENT, TISSUE AND ORGAN NAVIGATION

(75) Inventors: Ruediger Marmulla, Heidelberg (DE); Tim Lueth, Berlin (DE)

(73) Assignee: LB Medical GmbH, Berlin (DE)

(*) Notice: Subject to any disclaimer, the term of this patent is extended or adjusted under 35 U.S.C. 154(b) by 450 days.

(21) Appl. No.: 10/149,721

(22) PCT Filed: Dec. 13, 2000

(86) PCT No.: PCT/EP00/12685

§ 371 (c)(1),
(2), (4) Date: Jun. 13, 2002

(87) PCT Pub. No.: WO01/43654

PCT Pub. Date: Jun. 21, 2001

(65) Prior Publication Data

US 2002/0183608 A1 Dec. 5, 2002

(30) Foreign Application Priority Data

Dec. 13, 1999 (DE) ............................... 199 60 020

(51) Int. Cl.
*A61B 5/05* (2006.01)
(52) U.S. Cl. .................. 600/429; 600/426
(58) Field of Classification Search .......... 600/429, 600/428, 427, 426, 425, 417, 130
See application file for complete search history.

(56) References Cited

U.S. PATENT DOCUMENTS

| | | | | |
|---|---|---|---|---|
| 3,871,133 A | * | 3/1975 | Ellingson, Jr. | 49/308 |
| 5,331,227 A | * | 7/1994 | Hawes | 326/37 |
| 5,389,101 A | | 2/1995 | Heilbrun et al. | 606/130 |
| 5,776,064 A | * | 7/1998 | Kalfas et al. | 600/414 |
| 5,792,147 A | | 8/1998 | Evans et al. | 606/130 |
| 5,891,034 A | * | 4/1999 | Bucholz | 600/426 |
| 5,921,992 A | | 7/1999 | Costales et al. | 606/130 |
| 5,961,456 A | * | 10/1999 | Gildenberg | 600/429 |

FOREIGN PATENT DOCUMENTS

WO    WO 99/21498    5/1999

* cited by examiner

*Primary Examiner*—Daniel Robinson
(74) *Attorney, Agent, or Firm*—Norris McLaughlin & Marcus PA

(57) ABSTRACT

The invention relates to a method and device for referencing between a data set, which describes geometrically the spatial model of a body, and the real physical environment in which the body is placed. A three-dimensional position reference body is used on the real body. The position reference body has one or more elementary bodies or markers whose 3-dimensional position can be detected with sensors and which define a fixed geometric reference with respect to the center of gravity of the body or to other body reference volumes. For registration, the position reference body and/or its elementary bodies are correlated in the data model and in the physical world.

17 Claims, 3 Drawing Sheets

Figur 1
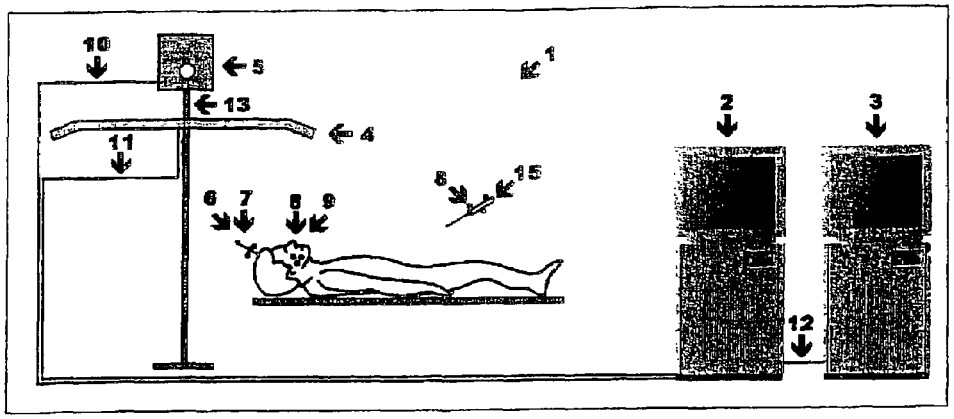
Figur 2
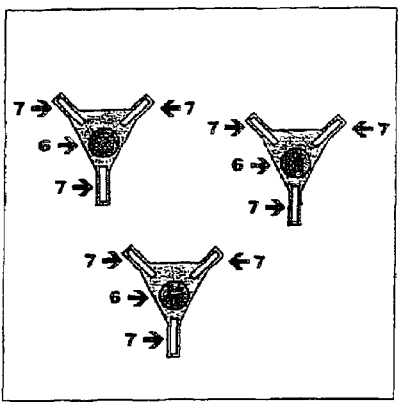
Figur 3
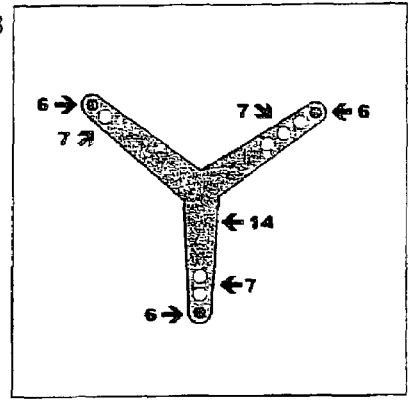
Figur 4
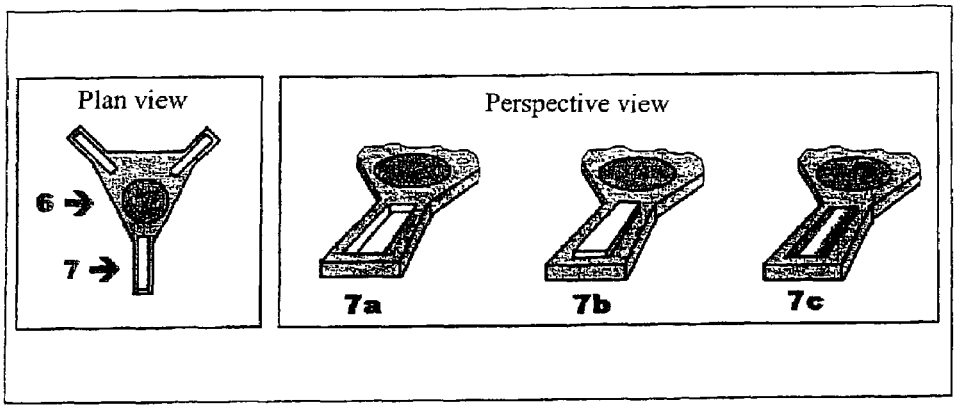
Figur 5
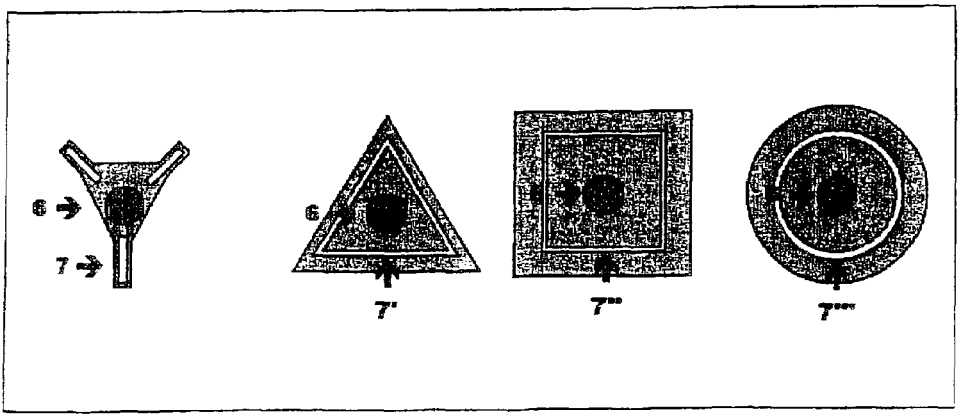

METHOD AND DEVICE FOR INSTRUMENT, BONE SEGMENT, TISSUE AND ORGAN NAVIGATION

BACKGROUND OF THE INVENTION

A patient data set and an operating site during surgery are typically referenced to each other by using either anatomical indicia or—before an image data set is created—implants (bone or skin markers) that are applied to the patient. The implants are indicated simultaneously with an input device at a workstation and with a localization system on the patient.

A more general task relates to referencing between a data set (which describes geometrically the spatial model of a body) and the real physical environment in which the actual body is placed. For referencing, a three-dimensional position reference body is used on or applied to the real body. The position reference body consists of one or more elementary bodies (markers) whose 3-dimensional position can be detected with sensors and which define a fixed geometric reference with respect to the center of gravity of the body or to other reference volumes of the body. For the purpose of registration, the position reference body and/or its elementary bodies are correlated in the data model and in the physical world.

Unlike the present method, the German patent DE 197 47 427 describes a method and a device wherein the characteristic surface of bone structures is used for providing a reference between a data set and the operating site. DE 197 47 427 describes an individual template which carries 3-D localization markers and is applied to and/or screwed on a bone segment.

The method has the disadvantage that an expensive CAD-CAM model has to be produced from a patient data set before an individual template can be manufactured. With many surgical procedures, large areas of bone have to be exposed for applying the individual surface template, which makes the procedure unnecessarily invasive.

SUMMARY OF THE INVENTION

It is an object of the present invention to provide a method and a device for instrument, bone segment, tissue and organ navigation, which operates without auxiliary devices, such as templates, and facilitates a safe and reproducible navigation.

By using optical measurements and by referencing the operating site via the characteristic surface of a soft tissue envelope or a bone surface, the cost can be reduced significantly and the surgical access path can be significantly less invasive. For a bone segment navigation with the present invention, the 3-D localization markers can be individually secured on a bone segment independent of a template—such as a screw, which opens additional possibilities for a minimally-invasive surgical procedure.

Optical referencing between the data set, the operating site and the 3-D localization markers is also faster and more precise than the aforedescribed referencing method that uses anatomical indicia and implants, because large surface structures in a patient data set (for example MRT or CT) can be imaged more exactly and reproduced than small, singular reference points.

BRIEF DESCRIPTION OF THE DRAWINGS

Embodiments of the invention are illustrated in the drawings and will be described hereinafter in more detail.

It is shown in

FIG. 1 a schematic diagram of the devices in an operating room,

FIG. 2 a detailed view of the 3-D reference markers with a device for detecting these markers by optical methods using 3-D scanners, FIG. 3 a geometric device for optical detection of 3-D reference markers, which are affixed to a frame, FIG. 4 a perspective view of the 3-D reference markers with associated geometric devices of different form (depression/sulcus, raised portion/crista, planar color-coded surface) for optical detection with the 3-D scanner, FIG. 5 alternative examples of different geometric forms that have a known spatial association with the 3-D marker, FIG. 6 additional coupled referencing markers, FIG. 7 an embodiment with a different coupling between the scanner and position detection unit, FIG. 8 referencing of bodies that do not necessarily have a stable form, and FIG. 9 device for positioning bodies that do not necessarily have a stable form.

DETAILED DESCRIPTION OF THE PREFERRED EMBODIMENTS

Figure 6:
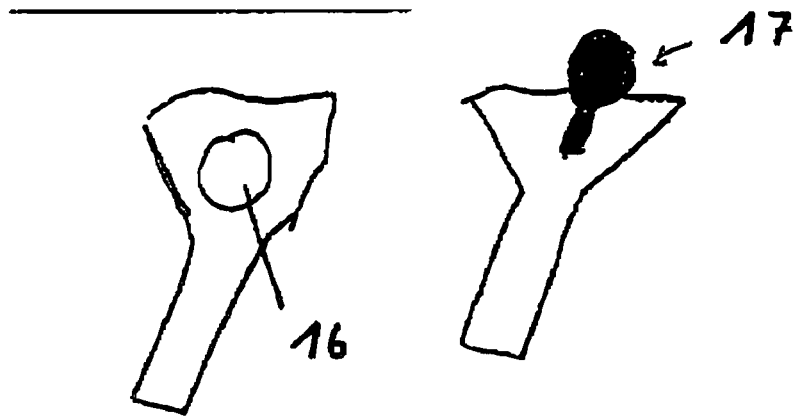

The invention will be described hereinafter in more detail with reference to a first embodiment.

The entire system 1 is used for optical referencing between an operating site, a patient data set and 3-D markers.

An optical 3-D scanner 5 is attached to a position detection unit 4 via a coupling device 13. The position detection unit 4 can acquire, for example, infrared signals, ultrasound signals or electromagnetic signals and allows the determination of three-dimensional coordinates of a corresponding 3-D marker 6 (for example: ultrasound transmitter, infrared transmitter, electromagnetic transmitter and/or reflectors 17 for all types of waves, ultrasound, infrared, radar, etc.). The 3-D scanner 5 (for example a 3-D laser scanner 5 or a radar unit 5a) can detect the shape and color of surfaces (for example 7), but not the signals from the 3-D markers 6. The signals from the 3-D markers 6 can be transmitted actively, for example with an LED, or passively, for example by using reflectors.

The data measured by the position detection unit 4 and the 3-D scanner 5 or the radar unit 5a are transmitted via a connection 10 and 11 to a display and processing unit 2. Since the position detection unit 4 and the 3-D scanner 5 are coupled via a connection 13 having a known geometrical relationship and/or are kinematically attached to each other via a connection 13, all coordinates measured with the position detection unit 4 can also be expressed in the coordinate system of the 3-D scanner 5 and vice versa.

A planning unit 3 is connected via 12 to the display and processing unit 2. Surgical procedures can be simulated on this planning unit 3; for example, resetting osteotomies can be planned before a bone segment navigation.

In this embodiment, at least three 3-D markers 6 are attached to the patient, which define a coordinate system on the patient. Geometric FIGS. 7 which can be detetced by the 3-D scanner 5, are arranged in a known, fixed spatial relationship to these 3-D markers 6. These FIGS. 7 can be implemented, for example, as a depression/sulcus 7a, a raised portion/crista 7*b,* as color-coded lines and fields 7*c* or as a bar code. The geometric FIG. 7 can also be in the form of a base on which a 3-D marker 6 is placed. The geometric FIG. 7 can also be formed directly by one or several 3-D markers 6.

The coordinates of the 3-D markers 6 can be uniquely determined by processing unit 2 from the geometry of the devices 7 by an inverse transformation. The geometry of these devices 7 can be different (7', 7", 7'''); it is only necessary that the geometry can be detected by the 3-D scanner 5 and that the processing unit 2 can determine the coordinates of the 3-D markers 6 from the geometry of the devices 7.

Figure 7:
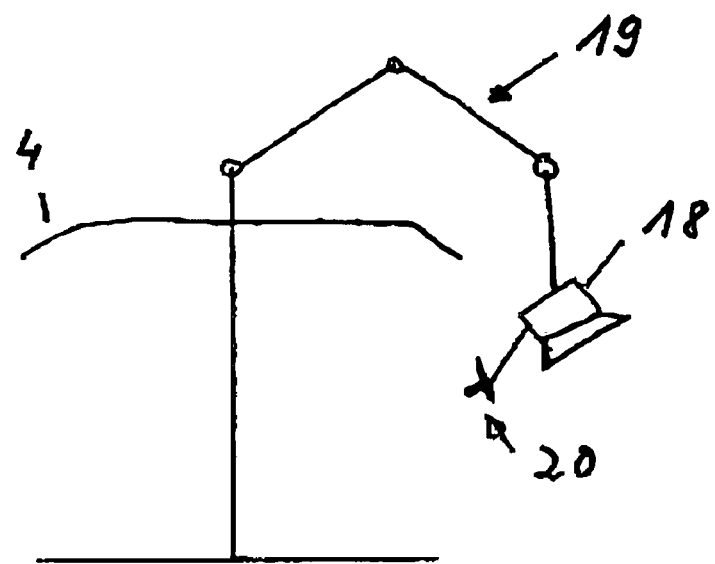

If the three 3-D markers 6 are fixedly connected with one another by a frame 14 in order to define a patient coordinate system, then the coordinates of the 3-D markers 6 can be determined by the processing unit 2 from the arrangement of the geometric FIGS. 7 on the frame 14. Alternatively, the scanner can also determine the coordinates directly by the analyzing the known geometries of the 3-D markers.

The operating site, the patient data set and the 3-D markers 6 are referenced to each other by first detecting with the 3-D scanner 5 the soft tissue (before the surgery, i.e., before the soft tissue swells or is displaced) or the bone surfaces 9 of the patient. The processing unit 2 processes the data from the 3-D scanner 5 and determines the most advantageous surface area fit between the patient and the patient data set. Thereafter, the patient and the patient data set can be referenced to each other by a coordinate transformation.

So far, however, the 3-D scanner 5 has not yet detected the 3-D markers 6. However, since the geometric devices 7 surrounding the 3-D markers 6 were scanned together with the patient and since the spatial relationship between the 3-D markers 6 and the geometric devices 7 is known, the coordinates of the 3-D markers 6 can be imaged both in the coordinate system of the data supplied by the 3-D scanner 5 as well as in the coordinate system of the patient data set.

Additional 3-D markers 8 which are either attached directly on a bone segment 9 or on a work tool 15 or coupled to these through a kinematic measurement mechanism or a coordinate measurement device, can subsequently be imaged in the patient data set on the display and processing unit 2.

In this way, a spatial displacement of a bone segment 9 that has been simulated on the planning unit 3, can also be reproduced on the patient.

Instead of coupling the 3-D scanner 5 and the 3-D marker position detection unit 4 through a fixed connection, the 3-D scanner 5 can also be flexibly coupled to the position detection unit 4 so as to be movable relative to the 3-D marker position detection unit 4, and can itself be provided with 3-D markers 8 for detection by the 3-D marker position detection unit 4.

FIG. 6 shows a 3-D marker 16 embodied as an LED and embodied as a passive reflector 17. The 3-D geometry of the bodies is sufficiently known and can therefore be used directly to uniquely determine the coordinates of the markers from the scanner data, without the need for additional encoding. The markers can be directly used as device geometries.

FIG. 7 shows an embodiment of a scanner 18 with a kinematic coordinate measurement device implemented as a measuring profile 19 and directly connected with the position detection unit. If necessary, the relative position of the scanner 18 can be determined by the second kinematic coordinate measurement device with significantly higher accuracy and measuring frequency. In an alternate embodiment, the base of the kinematic coordinate measurement device itself can be provided with a position reference body 20. In the simplest case, the kinematic coordinate measurement device is a simple body (for example a rod) of known geometry. Advantageously, the kinematic coordinate measurement device can also be attached to a table or applied directly on the patient, depending of which relative accuracy between the markers and the body should be optimized.

Figure 8:
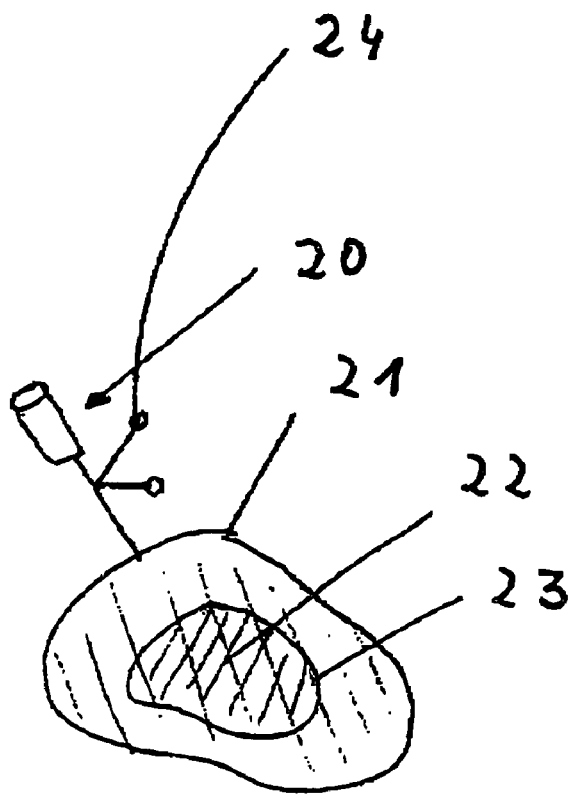

FIG. 8 shows instead of a bone (hard tissue) a more typical situation involving tissue that does not necessarily have a stable form, and/or an arbitrary body 21. In the simplest case, a relationship is established via a center of a gravity 22 of the body or another reference volume 23. This is advantageous when the method is to be applied also to soft tissue, organs or implants during alignment, transplantation and implementation. Even if perfect dimensional stability is not achieved, the method and device can still assist with navigation. Elementary bodies 24 are arranged on the position reference body 20*b*.

Figure 9:
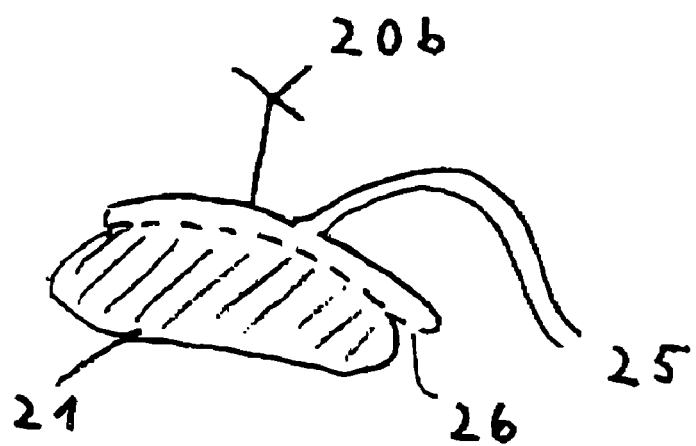

FIG. 9 shows a device for affixing the position reference bodies 20*b* to bodies 21 that may lack dimensional stability. The position reference body 20*b* is hereby attached to a mechanism that is disposed on the body 21 that lacks dimensional stability. In the depicted example, body tissue is drawn in by a reduced pressure process through a lumen 25 and through a membrane 26 and pressed into a predefined form. This form can advantageously have a shape that facilitates, for example, placement during transplantation or implantation. Other methods for affixing the tissue to the device, for example with adhesive, burrs or stitches, are also feasible.

The invention claimed is:

1. A method for instrument and bone segment as well as tissue and organ navigation, comprising the steps of: detecting position data of position reference bodies arranged on bones, tissue or organs and contour data and/or surface data of geometric figures arranged on or spatially correlated with the position reference bodies, and mathematically processing the data in such a way that the position data and the contour and/or surface data can be represented in a common coordinate system.

2. The method according to claim 1, wherein the position reference bodies define a fixed geometric reference relative to the center of gravity of the body or other body reference volumes and that for the purpose of registration, the position reference body or its elementary bodies are associated with each other in a data model and in the physical world.

3. A device for instrument and bone segment as well as tissue and organ navigation, comprising
   a 3-D marker position detection unit for detecting signals from 3-D markers, the 3-D marker position detection unit being coupled to an optical 3-D scanner or radar unit for detecting surfaces; and a geometric figure arrangement being one or both of at least one geometric figures connected with each of said 3-D markers or at least one 3-D markers shaped as a geometric figures, wherein the geometric figure is detectable by the 3-D scanner, thereby allowing a determination of the coordinates of the 3-D markers on the display and processing unit.

4. The device according to claim 3, wherein the display and processing unit
   enables referencing between an operating site and a patient data set through a computational surface fit and enables referencing between data of the 3-D position detection unit and data of the 3-D scanner based on the geometric figure arrangement.

5. The device according to claim 3, further comprising second 3-D markers for application on a bone segment of a patient or on an instrument for enabling a bone segment navigation or instrument navigation.

6. The device according to claim 3, wherein the geometric figures are applied to or on a frame connecting a plurality of 3-D markers.

7. The device according to claim 3, wherein a base, on which a 3-D marker is placed, is provided as the geometric figure for determining coordinates of the 3-D markers on the display and processing unit from 3-D scanner measurement data.

8. The device according to claim 6, wherein the frame forms the geometric figure for determining coordinates of the 3-D markers on the display and processing unit from 3-D scanner (5) measurement data.

9. The device according to claim 3, wherein at least one of said geometric figures is formed as one chosen from the group consisting of a recess/sulcus, a raised portion/crista (7b) and a sphere.

10. The device according to claim 3, wherein at least one of said geometric figures is color-coded or formed as a bar code.

11. The device according to claim 3, wherein at least two of the geometric figures are different from each other.

12. The device according to claim 3, wherein the coupling between the 3-D marker position detection unit and the 3-D scanner or the radar unit is a fixed connection.

13. The device according to claim 3, wherein the coupling between the 3-D marker position detection unit and the 3-D scanner or the radar unit is a connection via a coordinate measuring arm.

14. The device according to claim 5, wherein the 3-D scanner is not rigidly coupled with the position detection unit, but remains mobile with respect to the 3-D marker position detection unit and is itself provided with the second 3-D markers so as to be able to be registered by the 3-D marker position detection unit.

15. The device according to claim 14, wherein the 3-D scanner is implemented as a hand-held 3-D scanner.

16. The device according to claim 3, wherein the 3-D scanner and the position detection unit use the same receiver components for detecting position information and 3-D information.

17. The device according to claim 16, wherein the 3-D scanner and the position detection unit use the same transmitter components for detecting position information and 3-D information, and/or process the same physical transmitter waves.

* * * * *